United States Patent
Sun et al.

(10) Patent No.: US 10,234,419 B2
(45) Date of Patent: Mar. 19, 2019

(54) STATIC DISK ELECTRODE FOR ELECTROPLATING BATH ANALYSIS

(71) Applicant: Hong Kong Applied Science and Technology Research Institute Company Limited, Hong Kong (HK)

(72) Inventors: Yaofeng Sun, Hong Kong (HK); Sha Xu, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 264 days.

(21) Appl. No.: 15/162,609

(22) Filed: May 23, 2016

(65) Prior Publication Data

US 2017/0336350 A1    Nov. 23, 2017

(51) Int. Cl.
| | |
|---|---|
| *G01N 27/416* | (2006.01) |
| *C25D 21/12* | (2006.01) |
| *G01N 27/30* | (2006.01) |
| *G01N 27/28* | (2006.01) |

(52) U.S. Cl.
CPC ......... *G01N 27/4166* (2013.01); *C25D 21/12* (2013.01); *G01N 27/30* (2013.01); *G01N 27/28* (2013.01)

(58) Field of Classification Search
USPC ......................................................... 204/409
See application file for complete search history.

(56) References Cited

U.S. PATENT DOCUMENTS

| | | |
|---|---|---|
| 4,696,103 A | 9/1987 | Behl et al. |
| 6,306,280 B1 | 10/2001 | Reipa et al. |
| 7,077,946 B2 * | 7/2006 | He ............... G01N 27/403 204/409 |
| 7,361,257 B2 | 4/2008 | Wang et al. |
| 7,435,320 B2 | 10/2008 | Han et al. |
| 7,508,223 B1 * | 3/2009 | Yang ............... G01N 17/02 324/700 |
| 8,142,640 B2 | 3/2012 | Pavlov et al. |

(Continued)

FOREIGN PATENT DOCUMENTS

| | | |
|---|---|---|
| CN | 2344774 Y | 10/1999 |
| CN | 1884111 A | 12/2006 |
| CN | 201644040 U | 11/2010 |

(Continued)

OTHER PUBLICATIONS

Electrochemical Methods (Copyright 1980 by John Wiley & Sons, Bard and Faulkner Eds.) (Year: 1980).*

(Continued)

*Primary Examiner* — Gurpreet Kaur
*Assistant Examiner* — Steven E Rosenwald
(74) *Attorney, Agent, or Firm* — Spruson & Ferguson (Hong Kong) Limited

(57) ABSTRACT

The presently claimed invention provides an electrochemical analytical apparatus for electrochemical bath analysis. The apparatus comprise a static electrode and a rotatable unit. As steady liquid flow can be generated on the electrolytic surface of the static electrode by the rotatable unit through rotation, the static disk electrode does not involve any movement during the bath analysis such that the design of the electrical contact in the electrode can be substantially simplified.

11 Claims, 6 Drawing Sheets

(56) References Cited

U.S. PATENT DOCUMENTS

2015/0167195 A1    6/2015  Sun et al.
2016/0033446 A1*   2/2016  McGuinness ....... B01F 13/0818
                                                      205/793

FOREIGN PATENT DOCUMENTS

| CN | 201935893 U |   | 8/2011  |              |
|----|-------------|---|---------|--------------|
| CN | 203117159 U |   | 8/2013  |              |
| CN | 103743798 A |   | 4/2014  |              |
| CN | 203672824 U |   | 6/2014  |              |
| CN | 203965383 U |   | 11/2014 |              |
| CN | 204165928 U |   | 2/2015  |              |
| CN | 104422721 A |   | 3/2015  |              |
| CN | 204656450   | * | 9/2015  | ............. B01F 13/08 |
| CN | 204656450 U |   | 9/2015  |              |
| EP | 0151926 A2  |   | 8/1985  |              |

OTHER PUBLICATIONS

First Office Action of CN201680000538.X issued by the State Intellectual Property Office of the PRC dated Apr. 4, 2018.
International Search Report and Written Opinion issued for PCT Application No. PCT/CN2016/083925 dated Oct. 8, 2016.

* cited by examiner (A)

(B)

STATIC DISK ELECTRODE FOR ELECTROPLATING BATH ANALYSIS

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to electrochemical bath analysis. More particularly, the present invention relates to a static electrode for electrochemical bath analysis.

BACKGROUND

Cyclic voltammetric stripping (CVS) analyzer with a rotating disk electrode (RDE) is an established method to evaluate the composition concentration in plating baths. The CVS applies a reversible potential sweep to firstly deposit metal onto the surface of the rotating disk electrode, and then strips the metal back into solution. These cycles of ramps in potential may be repeated as many times as desired. The current at the working electrode is plotted versus the applied voltage to give a cyclic voltammogram trace.

The rotating disk electrode rotates during experiments and induces a flux of analyte to the electrode. The electrode includes a conductive disk embedded in an inert non-conductive polymer or resin that can be attached to an electric motor providing fine control of the electrode's rotation rate. The disk is mostly made of a noble metal or glassy carbon. As the disk turns, some of the solution is dragged by the spinning disk and the resulting centrifugal force flings the solution away from the center of the electrode. Solution flows up, perpendicular to the electrode, from the bulk to replace the boundary layer as shown in FIG. 1A. It results a laminar flow of solution towards and across the electrode. The rate of the solution flow can be controlled by the electrode's angular velocity and modeled mathematically. This flow can quickly achieve conditions in which the steady-state current is controlled by the solution flow rather than diffusion.

Nevertheless, as the electrode has to be rotated during analysis, a simple electrical wire, connecting the conductive disk and CVS analyzer for transmitting current, can not be used since the electrical wire is twisted under rotation. Thus, special design of the electrical contact has to be used. To solve this problem, the electrical contact is designed as shown in FIG. 1B. A conventional RDE 100 comprises a brush contact 101, a lower bearing assembly 102, a motor coupling 103, an attachment structure 104, and an electrode shaft 105. The brush contact 101 is a spring-loaded silver-carbon brush providing electrical contact with the rotating electrode shaft 105. The lower bearing assembly 102 can stabilize the rotating electrode shaft 105 at the point where the electrode shaft 105 exits a motor unit. The motor coupling 103 is used to attach the electrode shaft 105 to the motor. The attachment structure 104 is used to attach the electrode shaft 105 to the motor and comprises hex screws located on either side of the motor coupling 103 and being tightened to hold the electrode shaft 105 inside the motor coupling 103. The top end of the rotating electrode shaft 105 is mounted in the motor coupling 104 and the active electrode surface is located at the bottom end of the electrode shaft 105. However, the drawbacks of such electrical contact using the brush contact and the electrically conductive electrode shaft are expensive due to precision rotating control parts required, and short working life due to rotation wearing at the rotating electric contact. Furthermore, it is also difficult to fabricate the electrical contact since vibration or drifting of the electrode pole frequently appears.

Therefore, there is an unmet need to provide an electrode for electrochemical bath analysis having simplified electrical contact design.

SUMMARY

Accordingly, the presently claimed invention provides an electrochemical analytical apparatus for electrochemical bath analysis.

According to an embodiment of the present invention, an electrochemical analytical apparatus for electrochemical bath analysis comprises: a static working electrode having at least one electrolytic surface for being inserted into a liquid electrolyte; a rotatable unit comprising at least one blade and located near the static working electrode for creating flow of the liquid electrolyte by rotation; and a control unit for controlling the rotation of the rotatable unit for arousing a relative motion between the electrolytic surface of the working electrode and a bulk portion of the liquid electrolyte.

Preferably, the aroused relative motion is symmetrical relative to the at least one electrolytic surface of the static working electrode.

Preferably, the static working electrode is connected with an electrical contact.

Preferably, the static working electrode is a disk electrode or a ring disk electrode.

Preferably, the rotatable unit is located along a vertical axis of the at least one electrolytic surface of the static working electrode and rotates above the at least one electrolytic surface of the static working electrode.

Preferably, wherein the rotatable unit further comprises two or more blades being symmetrically arranged relative to the at least one electrolytic surface of the static working electrode.

Preferably, the control unit controls rotation speed of the rotatable unit.

Preferably, the rotatable unit is a magnetic stir bar freely mounted on a body of the static working electrode, and the control unit is a magnetic stirrer detachably coupled to the magnetic stir bar.

Preferably, the rotatable unit and the control unit are integrated into a motorized system.

According to a specific embodiment of the present invention, an electrochemical analytical apparatus for electrochemical bath analysis comprises: a static working electrode having at least one electrolytic surface located at bottom of the static working electrode for being inserted into a liquid electrolyte; an electrical contact connected to the static working electrode for transmitting current; a magnetic stir bar comprising a hole and at least two blades and located on top of the electrolytic surface for creating flow of the liquid electrolyte by rotation, wherein the hole is for accommodating the static working electrode, and the at least two blades are arranged in a symmetrical way to each other; and a magnetic stirrer for generating electric filed for controlling the rotation of the magnetic stir bar to arouse a relative motion between the electrolytic surface of the static working electrode and a bulk portion of the liquid electrolyte; wherein the aroused relative motion is symmetrical relative to the at least one electrolytic surface of the static working electrode.

According to another specific embodiment of the present invention, an electrochemical analytical apparatus for electrochemical bath analysis comprises: a static working electrode having at least one electrolytic surface located at bottom of the static working electrode for being inserted into a liquid electrolyte; an electrical contact connected to the static working electrode for transmitting current; and a motorized stirrer comprising a motor, a hole and at least two blades and located on top of the electrolytic surface for creating flow of the liquid electrolyte by rotation to arouse a relative motion between the electrolytic surface of the static working electrode and a bulk portion of the liquid electrolyte, wherein the motor is for driving the rotation of the motorized stirrer, and the hole is for accommodating the static working electrode, and the at least two blades are arranged in a symmetrical way to each other; wherein the aroused relative motion is symmetrical relative to the at least one electrolytic surface of the static working electrode.

As steady liquid flow can be generated on the electrolytic surface of the static electrode by the rotatable unit through rotation, the static disk electrode does not involve any movement during the bath analysis such that the design of the electrical contact in the electrode can be substantially simplified.

BRIEF DESCRIPTION OF THE DRAWINGS

Embodiments of the present invention are described in more detail hereinafter with reference to the drawings, in which.

DETAILED DESCRIPTION

In the following description, an electrochemical analytical apparatus for electrochemical bath analysis is set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

The foregoing description of the present invention has been provided for the purposes of illustration and description. It is not intended to be exhaustive or to limit the invention to the precise forms disclosed. Many modifications and variations will be apparent to the practitioner skilled in the art.

Figure 1A:
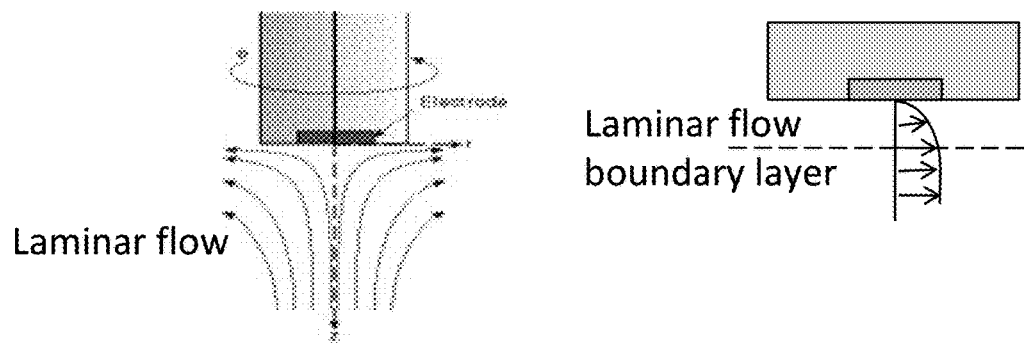
FIG. 1A depicts solution flow under the operation of a conventional rotating disk electrode.
Figure 1B:
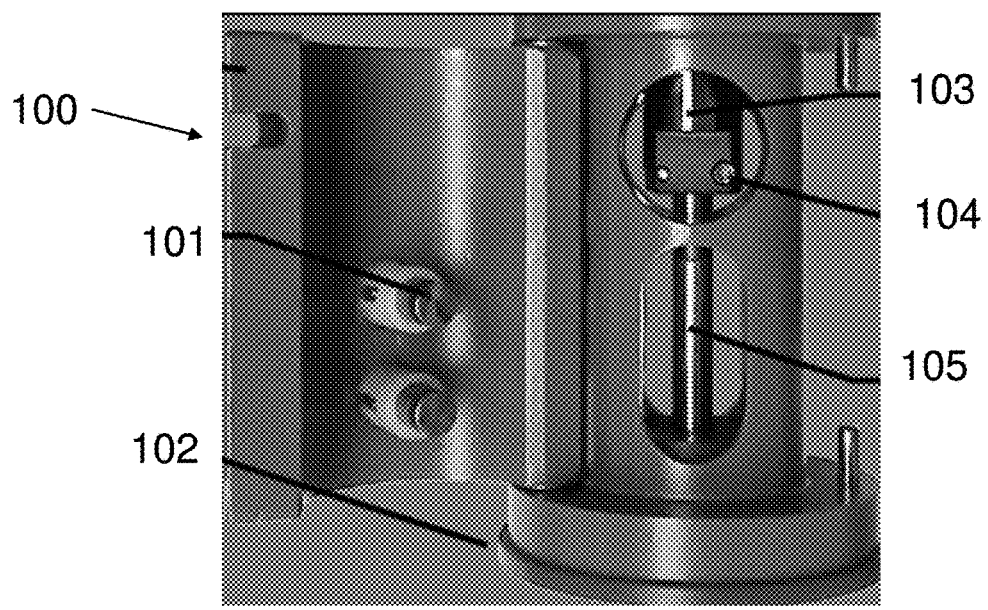
FIG. 1B depicts an electrical contact design of a conventional rotating disk electrode.
Figure 2A:
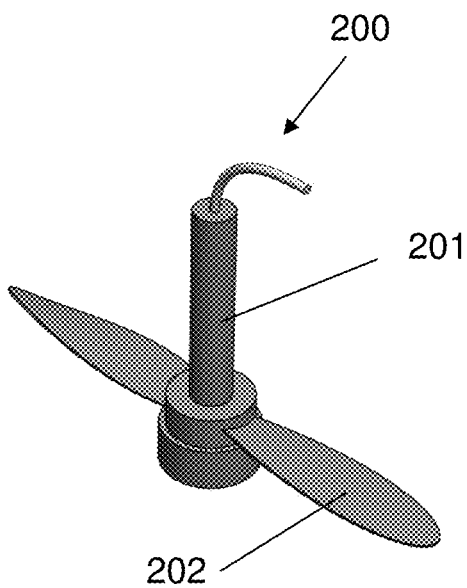
FIG. 2A depicts a electrochemical analytical apparatus with a magnetic stir bar according to an embodiment of the presently claimed invention.
Figure 2B:
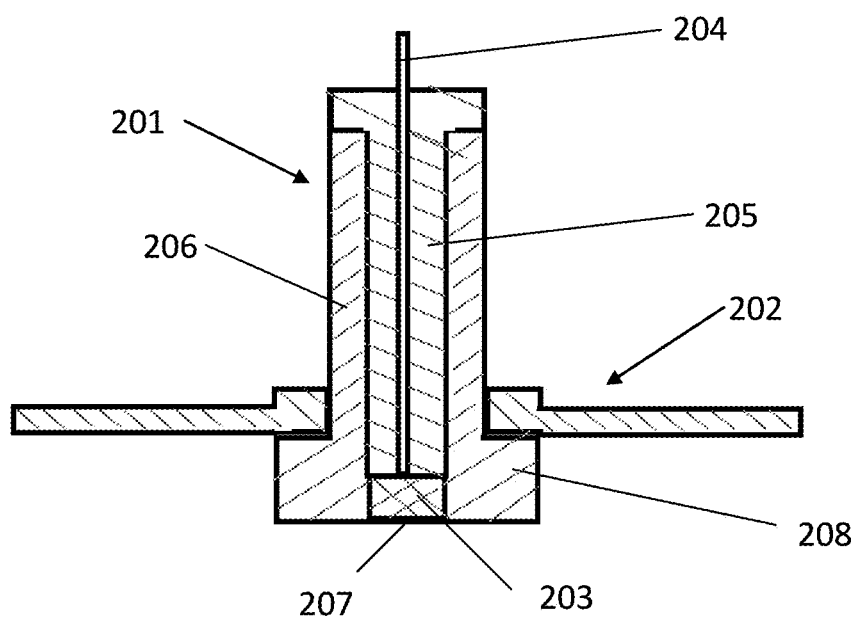
FIG. 2B depicts a cross section of the electrochemical analytical apparatus of FIG. 2A.
Figure 2C:
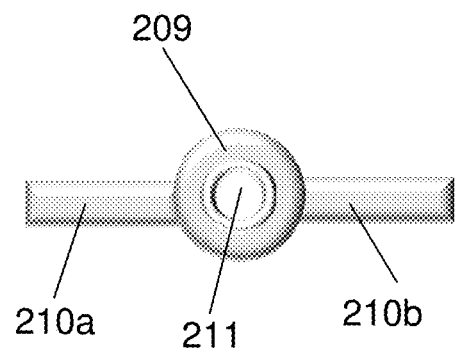
FIG. 2C depicts the magnetic stir bar of FIG. 2A.

FIG. 2A depicts an electrochemical analytical apparatus with a magnetic stir bar according to an embodiment of the presently claimed invention. The electrochemical analytical apparatus 200 comprises a static disk electrode 201 and a magnetic stir bar 202. FIG. 2B shows a cross section of the apparatus 200. The static disk electrode 201 comprises a disk electrode 203, an electrical contact 204, an electrode support 205, and an inert material sheath 206. The disk electrode 203 has an electrolytic surface 207 located at the bottom of disk electrode 203 for exposing to a liquid electrolyte. The electrical contact 204 is connected to the disk electrode 203 for transmitting current. The electrode support 205 is in contact with the disk electrode 203 and encloses the electrical contact 204 for provide structural support of the static disk electrode 201. The inert material sheath 202, being cylindrical, encloses both of the disk electrode 203 and the electrode support 205, and comprises an extending structure 208 for holding the magnetic stir bar 202. As shown in FIG. 2C, the magnetic stir bar 202, made from a magnetic material, comprises a connecting structure 209 and two blades 210a, 210b. The connecting structure 209 has a circular hole 211 located at the center of the connecting structure 209 for accommodating the cylindrical inert material sheath 206. The two blades 210a, 210b are connected with the connecting structure 209 in a symmetrical way and arranged in parallel to the electrolytic surface 207 for generating steady liquid flow. The rotation center of the rotatable unit 202 is located along the vertical axis of the center of the electrolytic surface 207 for providing symmetrical liquid flow on the electrolytic surface 207.

Figure 2D:
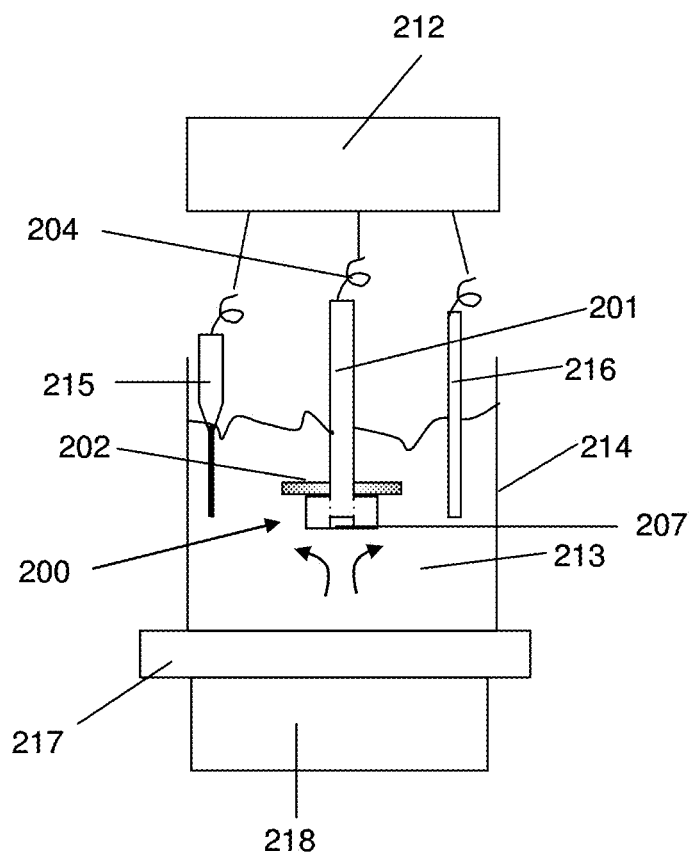
FIG. 2D depicts operation of the electrochemical analytical apparatus of FIG. 2A.

FIG. 2D depicts the operation of the apparatus 200. The apparatus 200 is connected to an electrochemical analyzer 212 in a three electrode system via the electrical contact 204. The apparatus 200 is inserted into a liquid electrolyte 213 in a tank 214. A reference electrode 215 and a counter electrode 216, connected with the electrochemical analyzer 212, are inserted into the liquid electrolyte 213. Then, the tank 214 is placed on a magnetic stirrer plate 217 of a magnetic stirrer 218. The magnetic stirrer 218 can generate rotating magnetic field by a rotating magnet or a set of stationary electromagnets. Once the magnetic stirrer 218 is switched on, the generated rotating magnetic field drives the magnetic stir bar 202 to rotate. The rotation of the magnetic stir bar 202 generates flow of the liquid electrolyte 213, which can create a relative motion symmetrically between the electrolytic surface 207 of the disk electrode 203 and a bulk portion of the liquid electrolyte 213. As the magnetic stir bar 202 is located on top of the electrolytic surface 207 in parallel with each other, the magnetic stir bar 202 is able to create a flow condition on the electrolytic surface 207 substantially similar to that created by the conventional rotating disk electrode. As such, a laminar flow of the liquid electrolyte 213 towards and across the electrolytic surface 207 is created. This flow can achieve a condition that a steady-state current is obtained, and mainly dictated by the solution flow rather than diffusion during chemical deposition. Under chemical deposition on the electrolytic surface 207 and the transmission of the corresponding current via the electrical contact 204, the composition concentration of the liquid electrolyte 213 can be evaluated. Meanwhile, since there is mutual magnetic attraction between the magnetic stir bar 202 and the magnetic stirrer 218, floating up of the magnetic stir bar 202 during rotation can be avoided such that the steady flow condition can be maintained.

Figure 3:
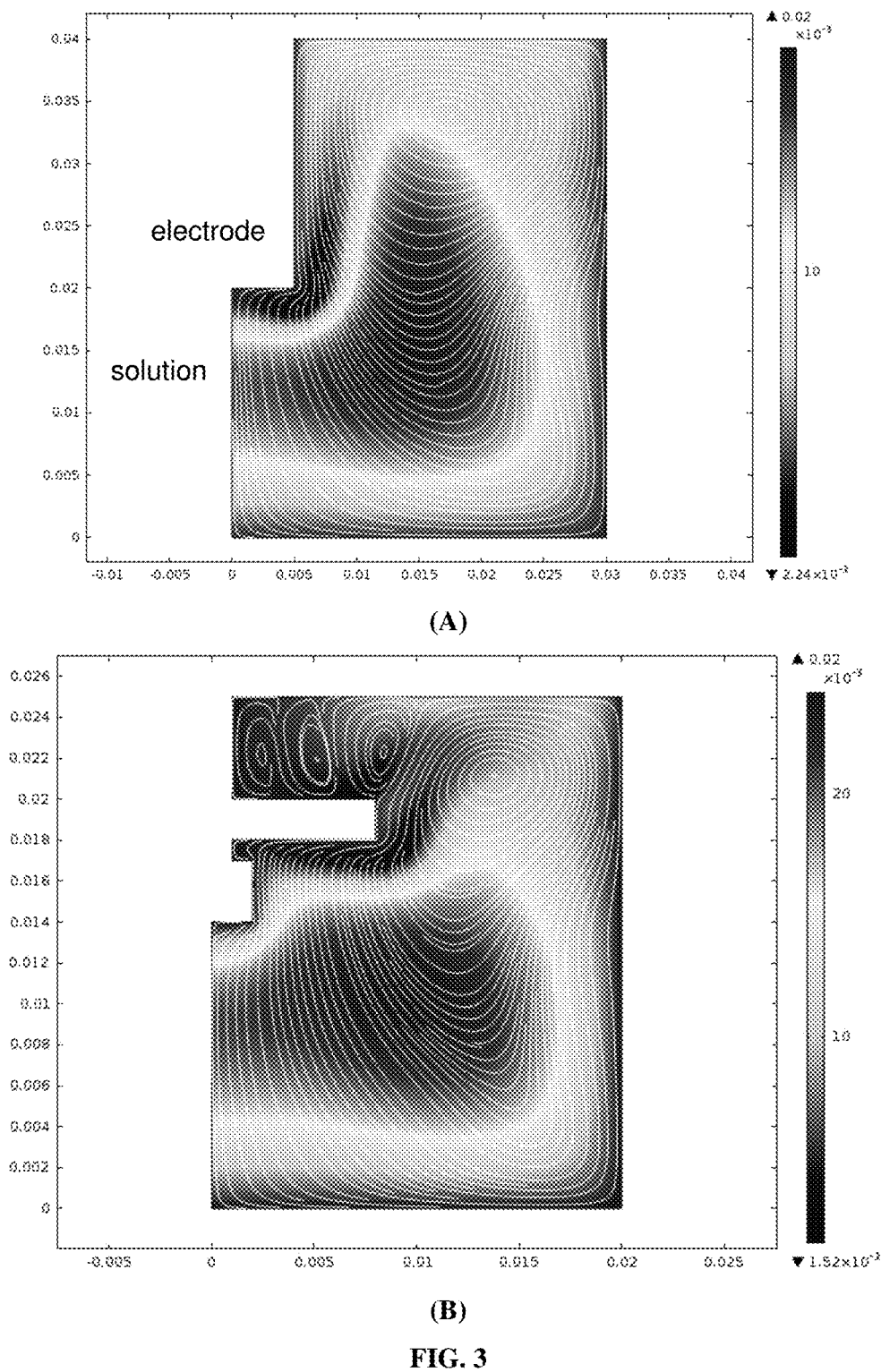
FIG. 3 depicts flow simulation results between (A) a convention rotating disk electrode and (B) an electrochemical analytical apparatus of the present invention respectively at 900 rpm.
Figure 4:
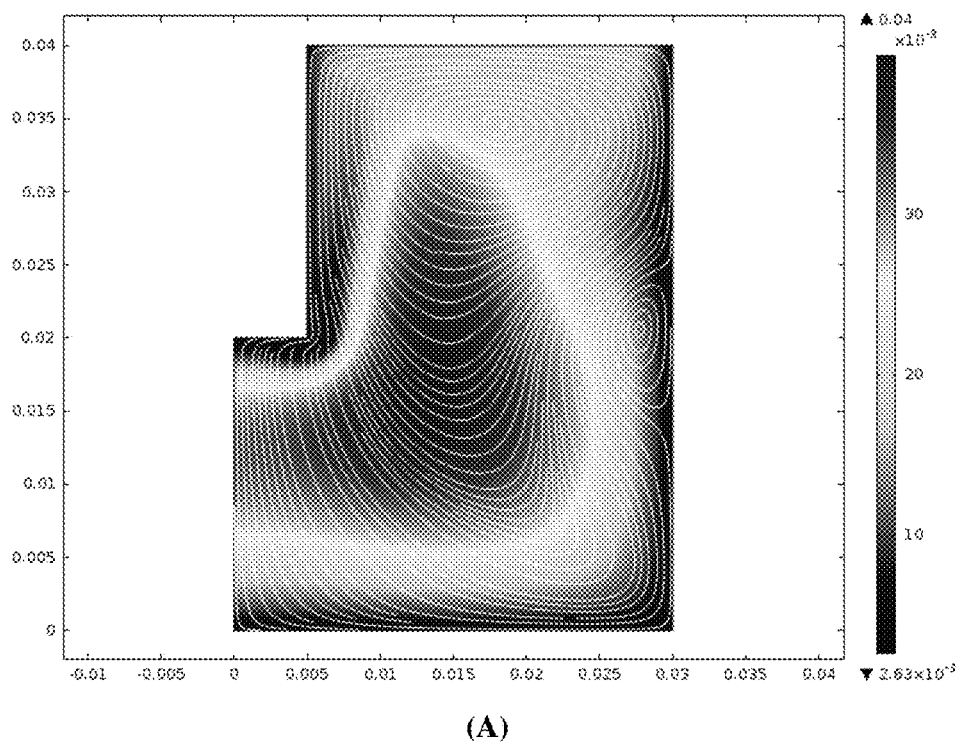
FIG. 4 depicts flow simulation results between (A) a convention rotating disk electrode and (B) an electrochemical analytical apparatus of the present invention respectively at 1500 rpm.
Figure 4:
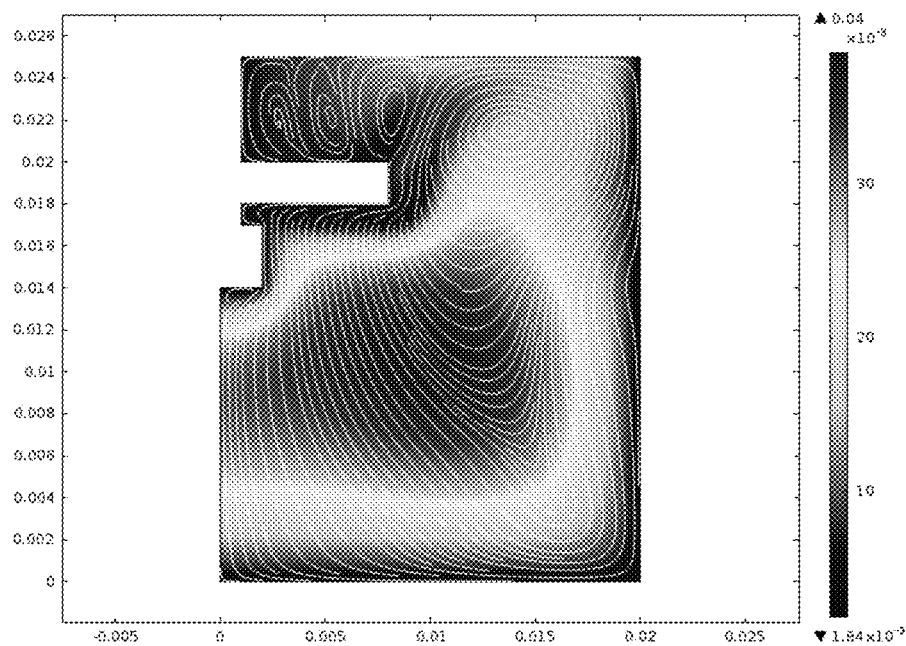

Flow simulation of the present invention is conducted to verify the corresponding performance. Several liquid flow simulations on an electrolytic surface are performed under a convention rotating disk electrode and the apparatus of the present invention at rotational speeds of 900 rpm and 1500 rpm respectively. As shown in FIGS. 3A-B, the simulation results show that the apparatus of the present invention is able to provide the flow condition similar to that of the traditional rotating disk electrode. Similarly, as shown in FIGS. 4A-B, the simulation results show that the apparatus of the present invention is also able to provide the flow condition similar to that of the traditional rotating disk electrode even at a higher rotational speed.

The rotational speed of the rotatable unit can be in a range of 50 to 1500 rpm, depending on the type of electrochemical bath to be analyzed. The rotation speed of the magnetic stirrer can be in a range of 0 to 1700 rpm. The rotatable unit, preferably, comprises from two to five blades being arranged in a symmetrical way such that the center of the gravity can keep at the center of the rotatable unit during rotation so as to avoid swinging, which may affect generation of steady liquid flow. The blade can be a straight blade or twisted blade for generating steady liquid flow. The electrical contact can be a simple electrical wire or a bundle of electrical wires for transmitting current since the electrode is always kept static during measurement. The shape of the static working electrode is cylindrical for holding the rotatable unit and facilitating its rotational movement.

According to the present invention, as the electrode provides static axis with electrical lines going through, the design of the electrical contact is substantially simplified, comparing with that of the rotating disk electrode. For example, a simple electrical wire, connected between the disk electrode and the chemical analyzer, is able to perform effective current measurement. The complex electrical contact mechanism required by the rotating disk electrode is avoided in the present invention.

Figure 5:
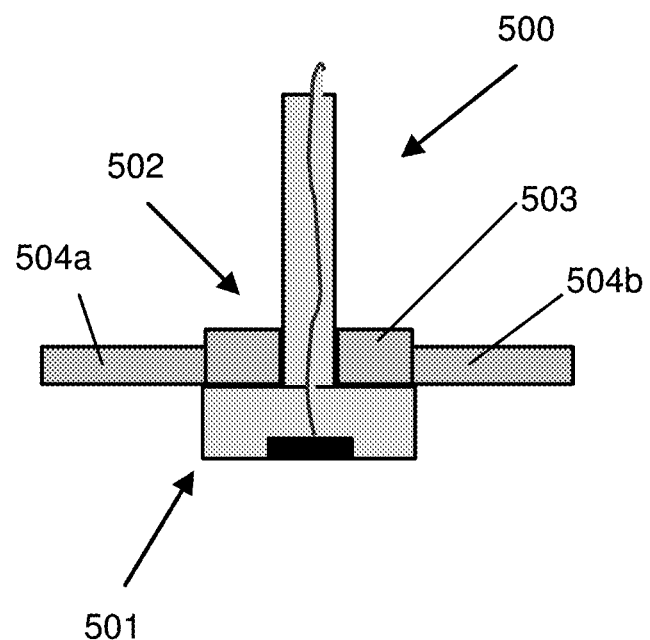
FIG. 5 depicts an electrochemical analytical apparatus with a motorized stirrer according to an embodiment of the presently claimed invention.

According to another specific embodiment of the present invention, an electrochemical analytical apparatus comprising a motorized stirrer is provided. As shown in FIG. 5, the apparatus 500 comprises a static disk electrode 501 and a motorized stirrer 502. The static disk electrode 501 is similar to that of FIG. 2A. The motorized stirrer 502 has a connecting structure 503 and two blades 504a, 504b, and further comprises a motor incorporated inside the connecting structure 503 to drive the rotation of the motorized stirrer 502. In this embodiment, there is no need to have an additional magnetic stirrer for driving the motorized stirrer, and plastic or metal blades can be used.

Figure 6:
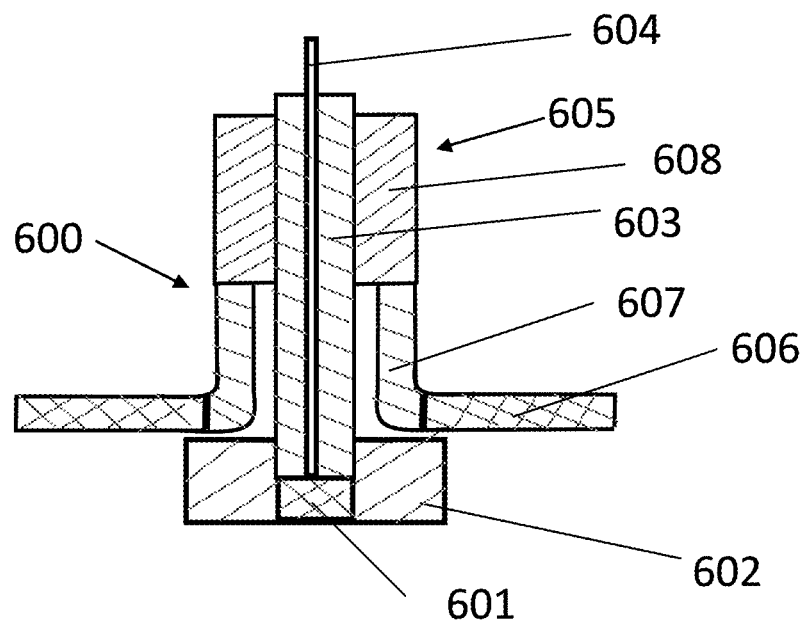
FIG. 6 depicts a cross section of an electrochemical analytical apparatus with a motorized stirrer according to another embodiment of the presently claimed invention.

As shown in FIG. 6, according to an embodiment of the present invention, an electrochemical analytical apparatus 600 comprises a disk electrode 601, an inert material sheath 602 of the electrode, a structural support 603 of the electrode, an electrical contact 604 of the electrode, and a motorized stirrer 605. The motorized stirrer 605 comprises blades 606, a connecting structure 607, and an electric motor 608. The connecting structure 607 connects the blades 606 and the motor 608 together. The motor 608 is mounted on the structural support 603, and located above the surface of an electrochemical bath during operation. The motor 608 can drive the blades 606 to rotate mechanically below the surface of the electrochemical bath.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An electrochemical analytical apparatus for electrochemical bath analysis, comprising:
a static working electrode having a body and at least one electrolytic surface for being inserted into a liquid electrolyte;
a rotatable unit comprising at least one blade and located concentrically with and near the static working electrode for creating a laminar flow of the liquid electrolyte towards the at least one electrolytic surface of the static working electrode; wherein the rotatable unit is freely mounted along a vertical axis of the body of the static working electrode and downstream from the at least one electrolytic surface of the static working electrode relative to the laminar flow; and
a control unit for controlling the rotation of the rotatable unit for arousing a relative motion between the electrolytic surface of the static working electrode and a bulk portion of the liquid electrolyte, wherein the laminar flow is symmetrical relative to the vertical axis of the body of the static working electrode.

2. The apparatus of claim 1, wherein the static working electrode is connected with an electrical contact.

3. The apparatus of claim 1, wherein the static working electrode is a disk electrode or a ring disk electrode.

4. The apparatus of claim 1, wherein the rotatable unit further comprises two or more blades being symmetrically arranged relative to the at least one electrolytic surface of the static working electrode.

5. The apparatus of claim 1, wherein the control unit controls rotation speed of the rotatable unit.

6. The apparatus of claim 1, wherein the control unit is a magnetic stirrer detachably coupled to the magnetic stir bar.

7. The apparatus of claim 1, further comprising a reference electrode and a counter electrode.

8. The apparatus of claim 1, wherein the at least one electrolytic surface is located at bottom of the static working electrode;
wherein the apparatus further comprises an electrical contact connected to the static working electrode for transmitting current;
wherein the magnetic stir bar comprises a hole and at least two blades and is located on top of the electrolytic surface, wherein the hole is for accommodating the static working electrode, and the at least two blades are arranged in a symmetrical way to each other; and
wherein the control unit comprises a magnetic stirrer for generating electric field for controlling the rotation of the magnetic stir bar;
wherein the aroused relative motion is symmetrical relative to the at least one electrolytic surface of the static working electrode.

9. The apparatus of claim 8, wherein the static working electrode is a disk electrode or a ring disk electrode.

10. The apparatus of claim 8, wherein the electrical contact is an electrical wire or a bundle of electrical wires.

11. The apparatus of claim 8, wherein a center of the magnetic stir bar is located along a vertical axis of the body.

* * * * *